United States Patent [19]

Chatterjee et al.

[11] Patent Number: 4,474,949
[45] Date of Patent: Oct. 2, 1984

[54] FREEZE DRIED MICROFIBRILAR CELLULOSE

[75] Inventors: Pronoy K. Chatterjee, Spotswood; Kambiz B. Makoui, North Brunswick, both of N.J.

[73] Assignee: Personal Products Company, Milltown, N.J.

[21] Appl. No.: 492,089

[22] Filed: May 6, 1983

[51] Int. Cl.³ ............................................... C08B 1/00
[52] U.S. Cl. ........................................ 536/56; 241/28; 241/DIG. 37; 604/364; 604/374; 604/904
[58] Field of Search ................. 536/56; 241/DIG. 37, 241/28; 604/364, 374, 904

[56] References Cited

U.S. PATENT DOCUMENTS

| | | | |
|---|---|---|---|
| 1,979,124 | 10/1934 | Tival | 241/DIG. 37 |
| 2,026,865 | 1/1936 | Campbell et al. | 536/56 |
| 3,067,037 | 12/1962 | Herald et al. | 536/56 |
| 3,157,518 | 11/1964 | Battista | 426/125 |
| 3,497,418 | 2/1970 | Thale et al. | 241/28 |
| 3,658,613 | 4/1972 | Steiger | 241/28 |
| 4,023,734 | 5/1977 | Hervé et al. | 241/DIG. 37 |
| 4,044,198 | 8/1977 | Kostrzewa et al. | 536/56 |
| 4,273,294 | 6/1981 | Hollely et al. | 241/DIG. 37 |
| 4,327,728 | 5/1982 | Elias | 604/904 |
| 4,357,467 | 11/1982 | Sachetto et al. | 536/56 |
| 4,374,702 | 2/1983 | Turbak et al. | 241/28 |
| 4,405,324 | 9/1983 | Cruz | 604/376 |

FOREIGN PATENT DOCUMENTS 1470825 9/1971 Fed. Rep. of Germany ........ 536/56

*Primary Examiner*—Ronald W. Griffin
*Attorney, Agent, or Firm*—Jason Lipow

[57] ABSTRACT

Absorbent retentive pulp, produced by mechanically treating a dispersion of cellulose fiber to the disintegrated and outer secondary walls to microfibrillar form. The beaten dispersion is then freeze dried.

18 Claims, 4 Drawing Figures

FREEZE DRIED MICROFIBRILAR CELLULOSE

BACKGROUND OF THE INVENTION

This invention relates to providing highly absorbent and retentive cellulose pulp and, in particular, providing such pulp for use in absorbent products such as sanitary napkins, catamenial tampons, diapers, dressings or the like which are used for absorbing body fluids.

Of course, it has been long known to utilize cellulose pulp for absorbing body fluids. Wood pump has been used for years in such products primarily because it is an inexpensive, readily available absorbent material. Such wood pulp is generally derived from soft wood trees such as southern pine and the like and is commercially treated in chemical pulping processes such as the kraft or sulfite processes during which the trunks and branches of trees are reduced to wood pulp fibers and non-fibrous substances such as gums, resins and lignin are chemically removed. The resulting wood pulp is sometimes bleached and then formed into board for subsequent disassociation into pulp fluff to be used in the aforementioned products.

It is also known that, in the commercial wet laid paper making process, pulp fibers may be mechanically treated, generally in a process step known in the art as beating, to generate some free microfibrils on the very outer layer of the pulp fibers. During the drying step, in such wet laid paper making processes, these freed microfibrils form hydrogen bonds with adjacent fibers and add, to a degree, to the stability of the finished paper sheet. Such beating operation, however, is not known to be employed in the art of producing pulp board for ultimately providing pulp fluff for absorbent products in that excessive hydrogen bonding is considered to be an adverse factor adding to the difficulty in grinding the pulp board into pulp fluff.

While, in the main, pulp fluff derived from the conventional process steps has been successfully employed in body fluid absorbent products, the art has increasingly sought to improve the absorption capacity and fluid retention properties of wood pulp. Many suggestions have already been put forth, generally directed toward chemical modifications of the cellulose polymer of which the wood pulp fibers are composed. While these efforts have met with some success, it can be generally stated that the resulting products are substantially more expensive than native wood pulp and suffer from some peculiar drawbacks such as brittleness, or slow wicking rates.

Accordingly, there is a need for a relatively inexpensive, simple process for treating native cellulose fibers to increase their absorption capacity and fluid retention properties.

SUMMARY OF THE INVENTION

In accordance with the teachings herein a highly absorbent, retentive, cellulosic fiber pulp is provided by a relatively simple process without the need of resorting to complicated and expensive chemical treatment.

Specifically, such absorbent, retentive pulp is produced by first forming a dilute aqueous dispersion of cellulose fibers. The dispersion is then mechanically treated (beaten) to a degree such that at least the outermost of the secondary walls of the cellulose fibers are essentially completely disintegrated to microfibrillar form. The beaten dispersion is then dried by the process of freeze drying whereby the water in the dispersion is first frozen by the application of refrigeration means and then the resulting ice is removed by sublimation, i.e., the ice is converted into the gaseous state without first passing into the liquid state and the gas is carried away leaving a substantially water free product. Sublimation of ice is accomplished generally by subjecting the frozen dispersion to a low pressure environment.

The resulting product is a cellulose pulp which has surprisingly increased absorption capacity and fluid retention as compared to that of conventionally derived cellulose pulp. Further, the structure of the cellulose pulp derived from the teachings of this invention is unique. Under microscopic observations, the fibrils released from the starting cellulose fibers by the beating step appear, after the dispersion is freeze dried, to be in the form of discrete platelets or sheets comprising said freed fibrils in compressed form. The sheets tend to appear as walls surrounding and defining cellular voids. Macroscopically, it is believed that this morphology results in the sponge-like appearance of the freeze dried pulp. It is also noted that while cells are apparently surrounded by sheet-like compressed microfibrils, the sheets are to some degree discontinuous and exhibit holes and, in general, resemble a leaf-like structure.

DETAILED DESCRIPTION OF THE INVENTION

Figure 1:
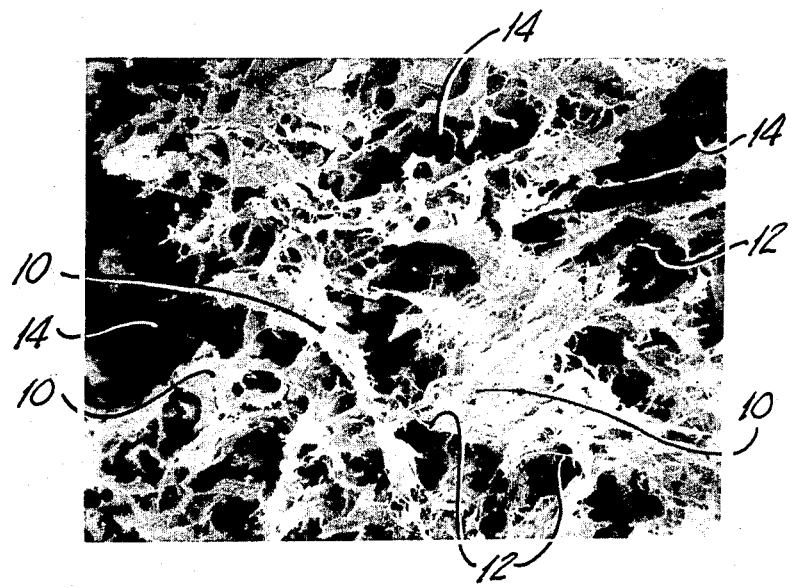
FIG. 1 is a scanning electron micrograph depicting the pulp of this invention at a magnification of 100 times.

In accordance with the invention an aqueous dispersion of fibrous cellulose is beaten to an extensive degree to free microfibrils from the fiberous structure.

While the preferred form of the starting cellulose fibers is chemical wood pulp derived from such pulping processes as kraft or sulfite pulping, it will be understood that almost any source of cellulose fibers is suitably employed. Accordingly, in addition to wood pulp, such diverse sources of cellulose fibers may include hemp, baggase, cotton and the like.

Irrespective of the plant source, cellulose fibers comprise cellulose chains, consisting of cellobiose units, laid down in a parallel arrangement with the long chained molecules strongly associated through secondary forces e.g. hydrogen bonds. This association of the cellulose chains results in a very uniform crystalline structure known as micelles or microcrystallites. The micelles are associated in the plant into long thread-like structures known as microfibrils. The association of the micelles into microfibrils is such that spaces or dislocations exist between micelles; such spaces, being of the order of about 15-20 angstrom units (A°), allowing liquid to migrate into the microfibril and accounting for at least part of the absorbency and retention properties of the cellulose fiber. High magnification photographs show that microfibrils of wood cellulose are filaments about 35 A° in breadth with a periodic variation in electron density along their lengths. Based on this observation, it has been proposed that the wood pulp microfibril is in the shape of a flat ribbon wound in the form of a tight helix.

The cellulose fiber itself is composed of layers of associated microfibrils. The outer layer is termed the primary wall and the inner layers are termed secondary walls which are further classified as $S_1$, $S_2$ layers, etc.

As described above, it is known, in the art of making paper, to beat or mechanically work a fiber slurry to free some microfibrils on the very outer layer of the cellulose fiber. The purpose of this beating treatment in the paper art is to enhance bonding. Great care, heretofore, has been taken to avoid damaging the inner layers.

In accordance with the teachings of this invention, such a beating step is carried further to the point where at least the outermost of the secondary walls is essentially completely disintegrated to microfibrillar form. Preferably, the starting cellulose fibers are first dispersed in a dilute aqueous slurry. Such a slurry should have a solid content ranging from about 0.5 to about 10.0% and still more preferably, from about 1.5 to about 6.0%.

The slurry is next passed to a beating station where it is mechanically worked to free microfibrils to the degree prescribed herein. The method and apparatus for beating the slurry in accordance with the teachings of the invention are not critical provided that the sufficient degree of microfibrillation is accomplished. Accordingly, commercially available equipment such as the Hollander, Jordan, or disk refiner type of beaters may be employed. The Hollander beater is an apparatus wherein the slurry is introduced into a tub and forced to pass under the nip formed between a corregated roller and a plate. As the roller is turned, a shearing force is exerted on the fibers in the nip. The Jordan type of beater employs two nesting cones with an annular space in between. The inner cone reciprocates so that the slurry, introduced into the annular space, is sheared. In the disk refiner, two round plates are in a face to face relationship and at least one of the plates is provided with ribs and at least one of the plates rotates. The slurry is introduced between the faces of the plates and is sheared by the rotating action. There exists still other suggestions for producing microfibrillar pulp and these are equally useful in carrying out this invention. One such suggestion is found in U.S. Pat. No. 4,374,702 issued on Feb. 22, 1983 to Turbak, et al.

It has been found that sufficient beating has occurred when the resulting fibers have been reduced to a Canadian Standard Freeness value of less than 100 and preferably less than 50. The period of time during which a slurry of a particular dilution, with a particular type of fiber is beaten in a particular beating apparatus is easily correlated to the Canadian Standard Freeness value of the finished product by a series of simple experiments. It will be understood that because the parameters which effect beating time may vary greatly and still produce a beaten slurry usable in accordance with the teachings of this invention, no generalization can be made with respect to such beating time. When using a Valey Beater, model 73-13-1 ½ Niagra, obtained from the Voith Company of Appleten, Wis. and beating a slurry of loblolly pine bleached kraft pulp having a solid content of 2%, suitable beating times ranged from 120 to about 160 minutes, which times may be considered exemplary.

Irrespective of the method of beating, the slurry may be thereafter concentrated, e.g., to about 4–10%, by filtering or suction means and then subjected to a freeze drying step. By freeze drying, it is meant that the slurry is subjected to refrigeration means sufficient to solidify the water therein. The frozen slurry is then subjected to conditions wherein the ice sublimates directly into the gaseous state without first passing through the liquid state and the gaseous water is removed.

Various means may be utilized for effecting the freezing step such as passing the slurry into an externally refrigerated compartment and retaining the slurry therein until frozen. Alternatively, the slurry may be circulated around a source of refrigeration such as cooling tubes or a bath containing coolant, e.g., liquid nitrogen, dry ice, alcohol solution, or the like and the frozen slurry collected.

To effect the sublimation and removal of water in the vapor phase, the frozen slurry is subjected to a subatmospheric pressure environment under which conditions water sublimates directly from the solid phase to the vapor phase. Vacuum means for providing such a subatmospheric pressure environment are well known in the art of freeze drying. Typically such subatmospheric pressure is less than about 5.0 Torr and preferably, less than about 0.5 Torr.

The resulting product is a sponge-like dried pulp which, either in this sponge-like state or when ground into pulp fluff, exhibits a substantial increase in liquid absorption and retention properties as contrasted with pulp provided by conventional means. While the precise reason for such unexpected improvement in absorption properties is not known, it appears to be a result of the unusual morphology resulting from preparing pulp by the teachings herein.

Figure 2:
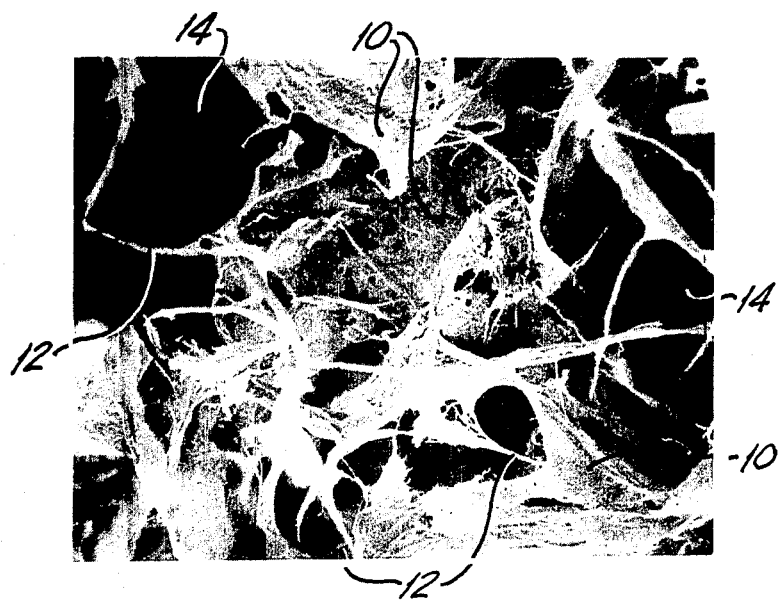
FIG. 2 is a micrograph of the pulp shown in FIG. 1 at a magnification of 1000 times.
Figure 3:
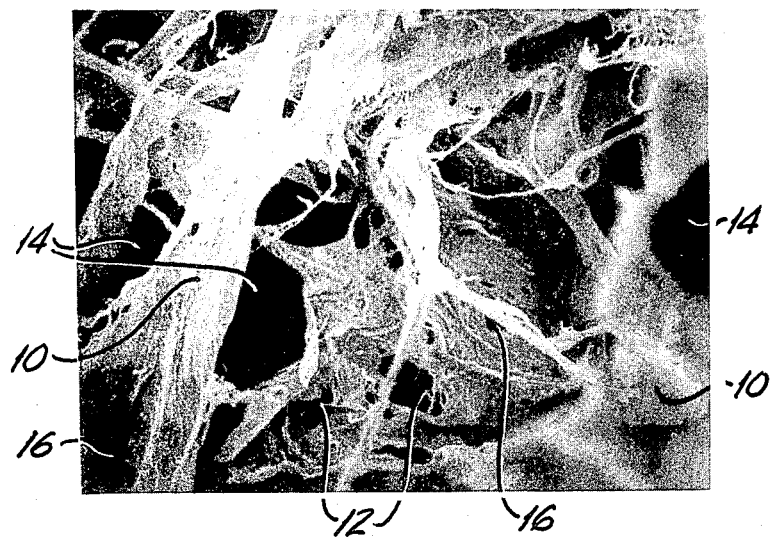
FIG. 3 is micrograph of the pulp shown in FIG. 1 at a magnification of 2000 times.
Figure 4:
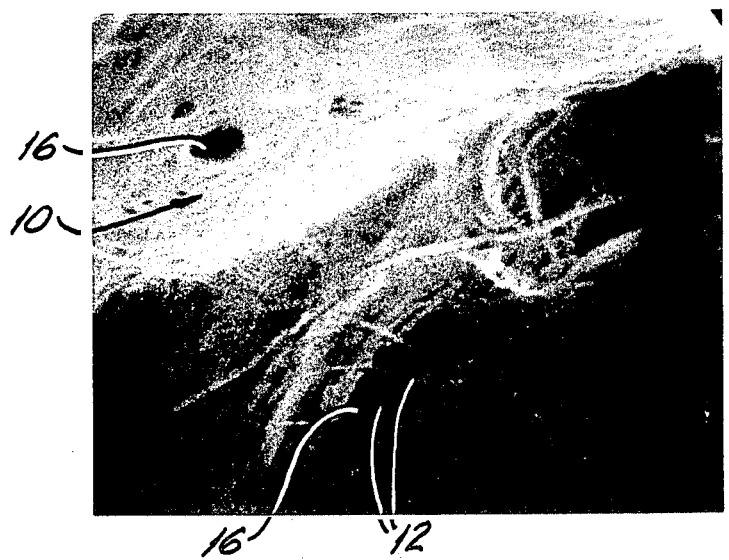
FIG. 4 is a micrograph of the pulp of FIG. 1 at a magnification of 20,000 times.

Referring now to the drawings, illustrated in FIGS. 1–4 are a series of Scanning Electron Micrographs of increasing magnification, depicting loblolly pine kraft pulp, beaten in a Valley beater for 160 minutes and then freeze dried. At these high magnifications, it can be seen that the pulp comprises sheets or platelets 10 of microfibrils 12. These sheets are of random shape and appear to form somewhat discontinuous walls surrounding voids 14. At the higher magnifications it can be seen that the platelets are almost leaf-like in structure and are fenestrated, as for example, fenestration 16.

As illustrated, the platelets vary in their largest dimension from about 2 microns to about 130 microns, with 70 microns being typical. The platelets are no more than about 5 microns thick and typically about 2 microns thick. The platelets surround void areas having a largest dimension value of less than about 500 microns.

Without being bound by any particular theory, it is believed that the unique morphology of the pulp of this invention results from the fact that when the fibrillated pulp is subjected to freezing, the growing, expanding ice crystals compress the fibrils between crystal facets into flat sheets. The sublimation process does not disturb this configuration, and instead, the ice, filling the volume between the compressed sheets of fibrils, vaporizes leaving behind the voids 14.

EXAMPLE 1

To illustrate the unique properties of the pulp of this invention, a series of pulp samples are prepared. In each case the starting cellulose fibers are loblolly pine bleached kraft wood pulp obtained from the International Paper Company of Panama City, Fla. A dilute dispersion of the pulp was prepared having a solid content of about 2% by weight in water. This dispersion was mechanically worked in a Valey Beater, Model No.

73-13-1½ Niagra obtained from the Voith Company of Appleton, Wis. The beating was carried out for the various time increments noted below in Table 1. The resulting beaten slurry was then freeze dried using a freeze drying apparatus obtained from New Brunswick Scientific Corporation of New Brunswick, N.J. The slurry is introduced into petry dishes which are then placed over granulated dry ice at an effective cooling temperature of about −78° C. The frozen slurry is then placed in the freeze drying apparatus and the water is removed by sublimation under a vacuum of 0.04 Torr. A first set of samples are ground after freeze drying in a hammer mill containing fixed hammers in a rotor. A second set of samples are maintained in the sponge-like state obtained from the freeze drying process.

The samples are tested for maximum capacity, fluid retention and time to absorb to maximum capacity by utilizing the Porous Plate Testing apparatus, as described in detail in Textile Res. J. 37 pp. 356–366, 1967. Briefly, this test involves placing the sample in what is essentially a Buchner Funnel having a porous bottom plate and holding the sample in place by applying thereon a standard weight to maintain a standardized confining pressure. The porous plate is placed in contact with a reservoir of fluid and the sample is allowed to absorb the fluid through the porous plate until saturated. By maintaining the samples at essentially the level of the reservoir, the fluid absorbed is subjected to essentially zero hydraulic head with respect to the reservoir. The volume of fluid absorbed, divided by the weight of the sample, is termed the Maximum Capacity. As the sample absorbs fluid, a measurement of volume absorbed as a function of time is made. The slope of this curve at the time absorption begins is termed the Initial Rate of Absorption. To determine fluid retention, the saturated sample is elevated with respect to the reservoir, thereby imposing a hydraulic head upon the fluid absorbed, the head being arbitrarily chosen as 35.5 cm. of fluid. The apparatus is provided with means for measuring the volume of fluid retained under the hydraulic head. Retention values are reported as the volume retained per unit weight of sample. The results of testing the samples are recorded below in Table 1. The testing fluid in each case is a 1% NaCl aqueous solution, and the confining pressure is 4.8 grams/cm$^2$.

(merely slurried and freeze dried but not fibrillated) reveals a marked improvement in absorption properties by incorporating the teachings of this invention.

A series of samples comprising the freeze dried fibriliated wood pulp of this invention are formed into compressed cylindrical tampons having a density of 0.02 grams per cubic centimeter. Additionally, control tampons comprising freeze dried chemical wood pulp are similarly formed into tampons of the same density. The capacity of the experimental and control tampons to absorb a one percent by weight aqueous sodium chloride solution under simulated in use conditions is determined by allowing one end of the tampon to be submerged in the liquid to be absorbed for a period of five minutes while maintaining the sides of the tampon under a confining pressure as set out in Table 2 below. The confining pressure is maintained by enveloping the tampon in a hydraulically inflated polyethylene sleeve. Excess fluid is drained from the tampon for a period of two minutes, the pressure is released, and the weight of the fluid absorbed by the tampon is determined and reported as Capacity, in units of weight of liquid absorbed per unit weight of the tampon.

TABLE 2

| | ABSORBENCY OF TAMPONS | | | |
|---|---|---|---|---|
| Confining Pressure (ins. of water) | Freeze-Dried Material | Beating Time (Min) | Density (g/cc) | Capacity g/g |
| 8 | Pulp (control) | 0 | .02 | 9.2 |
| | Microfibrillated | 160 | .02 | 12.3 |
| 24 | Pulp (control) | 0 | .02 | 6.6 |
| | Microfibrillated | 160 | .02 | 6.5 |

As can be seen from Table 2, at a confining pressure of 8 inches of water, the microfibrillated freeze dried wood pulp of this invention exhibits a substantial increase in capacity over the control chemical wood pulp tampon. On the other hand, it is evident that at higher confining pressures, the two tampons are essentially equivalent in capacity.

While the invention has been described in terms of producing a highly absorbent cellulose pulp, nothing herein should be construed to suggest that the cellulose fibers cannot be otherwise additionally treated by, for example, chemical means to further enhance absor-

TABLE 1

| | | ABSORBENCY OF FREEZE DRIED MICROFIBRILLAR WOOD PULP | | | | |
|---|---|---|---|---|---|---|
| Canadian Standard Freeness | Beating Time (min) | Sample Form | Bulk Density (g/cm$^3$) | Slope of Curve Initial Rate of Abs. (cc/min) | Maximum Abs. (g/g) | Retention (g/g) |
| 700 | 0 | Unground Disk | .02 | 3 | 13 | 3 |
| 500 | 23 | " | .02 | 5 | 15 | 2 |
| 300 | 36 | " | .02 | 6 | 17 | 3 |
| 100 | 56 | " | .02 | 7 | 16 | 3 |
| 0 | 91 | " | .02 | 9 | 17 | 5 |
| 0 | 120 | " | .02 | 11 | 21 | 7 |
| 0 | 140 | " | .02 | 12 | 21 | 8 |
| 0 | 160 | " | .01 | 13 | 21 | 9 |
| 700 | 0 | Ground Disk | .03 | 5 | 11 | 2 |
| 500 | 23 | " | .04 | 7 | 13 | 3 |
| 300 | 36 | " | .04 | 11 | 12 | 3 |
| 100 | 56 | " | .04 | 11 | 13 | 4 |
| 0 | 91 | " | .04 | 11 | 12 | 5 |
| 0 | 120 | " | .04 | 13 | 14 | 6 |
| 0 | 140 | " | .04 | 13 | 14 | 7 |
| 0 | 160 | " | .03 | 13 | 15 | 9 |

As can be seen from Table 1, a comparison of the fibriliated freeze dried samples with the control sample bency. Similarly the cellulose of this invention, may be combined with other components to produce a composite material for absorbent purposes. Such modification, as well as others which will occur to one skilled in the art, are all within the scope and teachings of this invention.

What is claimed is:

1. An absorbent product comprising as an absorbent element therein fibrous cellulose pulp having been beaten and freeze dried, said beaten, freeze dried cellulose pulp comprising sheet like particles of microfibrils, said sheet like particles arranged as discontinuous walls surrounding void volumes.

2. The absorbent product of claim 1 wherein said beaten, freeze dried cellulose pulp has a Porous Plate Capacity of at least 15 g/g with a testing fluid of 1% NaCl aqueous solution.

3. The absorbent product of claim 1 wherein said beaten, freeze dried cellulose pulp has a Porous Plate Retention of at least 10 g/g with a testing fluid of 1% NaCl aqueous solution under a hydraulic head of 35.5 cm of liquid.

4. The absorbent product of claim 1 wherein said beaten, freeze dried cellulose pulp comprises said sheets having a largest dimension of from about 2 microns to about 130 microns and a thickness of less than five microns.

5. The absorbent product of claim 1 wherein said product is a sanitary napkin.

6. The absorbent product of claim 1 wherein said product is a catamenial tampon.

7. The absorbent product of claim 1 wherein said product is a disposable diaper.

8. The absorbent product of claim 1 wherein said product is a wound dressing.

9. The product of claim 1 wherein the starting cellulose fibers are wood pulp.

10. An absorbent product comprising as an absorbent element therein highly absorbent, retentive cellulose pulp, said cellulose pulp having been provided by:
forming a dilute aqueous dispersion of cellulose fibers;
extensively beating said slurry to a degree such that at least the outermost of the secondary walls of said cellulose fibers are essentially completely disintegrated into microfibrillar form; and
freeze drying said slurry;
whereby said highly absorbent, retentive cellulose pulp results.

11. The product of claim 10 wherein said aqueous dispersion has a solid content ranging from about 0.5 to about 10.0% solids, by weight.

12. The product of claim 11 wherein said aqueous dispersion has a solid content ranging from about 1.5 to about 6.0% solids, by weight.

13. The product of claim 10 wherein beating is carried out to an extent to reduce said cellulose fibers to a Canadian Standard Freeness value of less than 100.

14. The product of claim 13 wherein beating is carried out to an extent to reduce said cellulose fibers to a Canadian Standard Freeness value of less than 50.

15. The product of claim 10 wherein said product is a sanitary napkin.

16. The product of claim 10 wherein said product is a catamenial tampon.

17. The product of claim 10 wherein said product is a disposable diaper.

18. The product of claim 10 wherein said product is a wound dressing.

* * * * *